United States Patent
Marshall et al.

(10) Patent No.: US 8,425,547 B2
(45) Date of Patent: Apr. 23, 2013

(54) DISPOSABLE SKIN PRICKER

(75) Inventors: Jeremy Marshall, Oxford (GB); Adam John Mumford, Oxford (GB)

(73) Assignee: Owen Mumford Limited, Oxfordshire (GB)

( * ) Notice: Subject to any disclaimer, the term of this patent is extended or adjusted under 35 U.S.C. 154(b) by 1215 days.

(21) Appl. No.: 10/547,127

(22) PCT Filed: Mar. 9, 2004

(86) PCT No.: PCT/GB2004/000966
§ 371 (c)(1),
(2), (4) Date: Apr. 18, 2006

(87) PCT Pub. No.: WO2004/080305
PCT Pub. Date: Sep. 23, 2004

(65) Prior Publication Data
US 2006/0253146 A1 Nov. 9, 2006

(30) Foreign Application Priority Data
Mar. 10, 2003 (GB) .................................. 0305363.4

(51) Int. Cl.
*A61B 17/32* (2006.01)
(52) U.S. Cl.
USPC ........................................................ 606/182

(58) Field of Classification Search .......... 606/181–185, 606/167; 600/583; 604/110, 111, 157, 192
See application file for complete search history.

(56) References Cited

U.S. PATENT DOCUMENTS

| 5,755,733 | A  | * | 5/1998 | Morita | 606/182 |
|---|---|---|---|---|---|
| 6,866,641 | B2 | * | 3/2005 | Marshall | 600/583 |
| 7,357,808 | B2 | * | 4/2008 | Kennedy | 606/181 |
| 2006/0047220 | A1 | * | 3/2006 | Sakata et al. | 600/583 |

FOREIGN PATENT DOCUMENTS

| WO | WO 02/43591 | 6/2002 |
|---|---|---|
| WO | 02065910 A1 | 8/2002 |

* cited by examiner

*Primary Examiner* — Kevin C Sirmons
*Assistant Examiner* — Kami A Bosworth
(74) *Attorney, Agent, or Firm* — Young & Thompson

(57) ABSTRACT

A lancet body for a skin pricker has resiliently flexible fingers (9) with outwardly splayed tips (10). The device is fired by pressing a trigger (13) and a spring (5) urges the lancet forwards and the fingers (9) flex inwards as the tips (10) snap past barbs (11), so that the tips (10) of the arms (9) engage behind the barbs (11). If the user tries to push the lancet back into the cocked condition, the fingers (9) are trapped and will flex as the tips (10) press against the barbs (11) until the arms buckle and the tips (10) are pushed out through openings (14). Thus the lancet is arrested and immobilized before a re-cocked position is reached, and re-firing is prevented.

10 Claims, 2 Drawing Sheets

DISPOSABLE SKIN PRICKER

BACKGROUND OF THE INVENTION

This invention relates to skin prickers. It is a development of that described in WO 02/043,591, which is concerned with ensuring that the lancet, once fired, cannot be pushed back via the needle tip aperture, re-cocked and re-fired. The present invention improves upon that design.

SUMMARY OF THE INVENTION

According to the present invention there is provided a disposable skin pricker comprising an elongate housing with a spring-loaded, longtiduinally movable lancet carried therein, the lancet tip normally being within the housing, a trigger mechanism to retain the lancet in a fully retracted position in which it energizes the spring, the trigger mechanism being actuable to release or fire the lancet to cause the tip to have a momentary position projecting from the forward end of the housing, and means for preventing repeated use including a spring finger extending rearwardly from the lancet alongside but spaced from the body thereof, and an abutment on the inside of the housing past which the tip of the finger will snap during forward motion of the lancet, any attempt to push the lancet back with a greater than a predetermined force after firing resulting in the abutment deflecting the finger tip out through an aperture in the side wall of the housing.

Preferably, the lancet is symmetrical, with two fingers on opposite sides thereof. The housing will then have two opposed apertures and abutments, and these abutments may be shaped as barbs pointing inwards and forwards.

In one form the or each finger inclines outwardly from the lancet body as well as extending rearwardly.

Alternatively the or each finger may be generally parallel to and spaced from the adjacent part of the body of the lancet but with its tip flaring outwardly.

The needle tip may initially be protected by an elongate cap by which the lancet can be pushed back to the fully retracted position from an initial pre-fired position wherein the or each finger tip is immediately to the rear of the associated abutment.

For a better understanding of the invention, one embodiment thereof will now be described, by way of example, with reference to the accompanying drawings, in which:

DETAILED DESCRIPTION OF THE INVENTION

Figure 1:
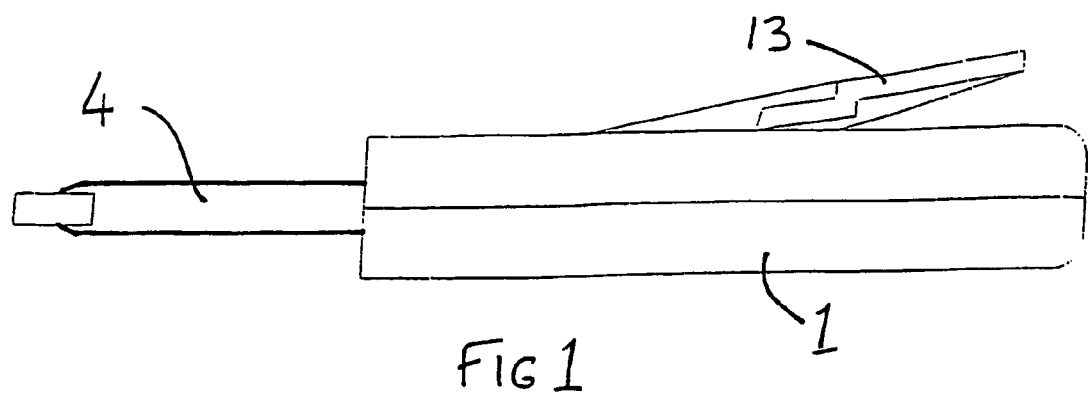
FIG. 1 is a side view of a skin pricker of the invention.
Figure 2:
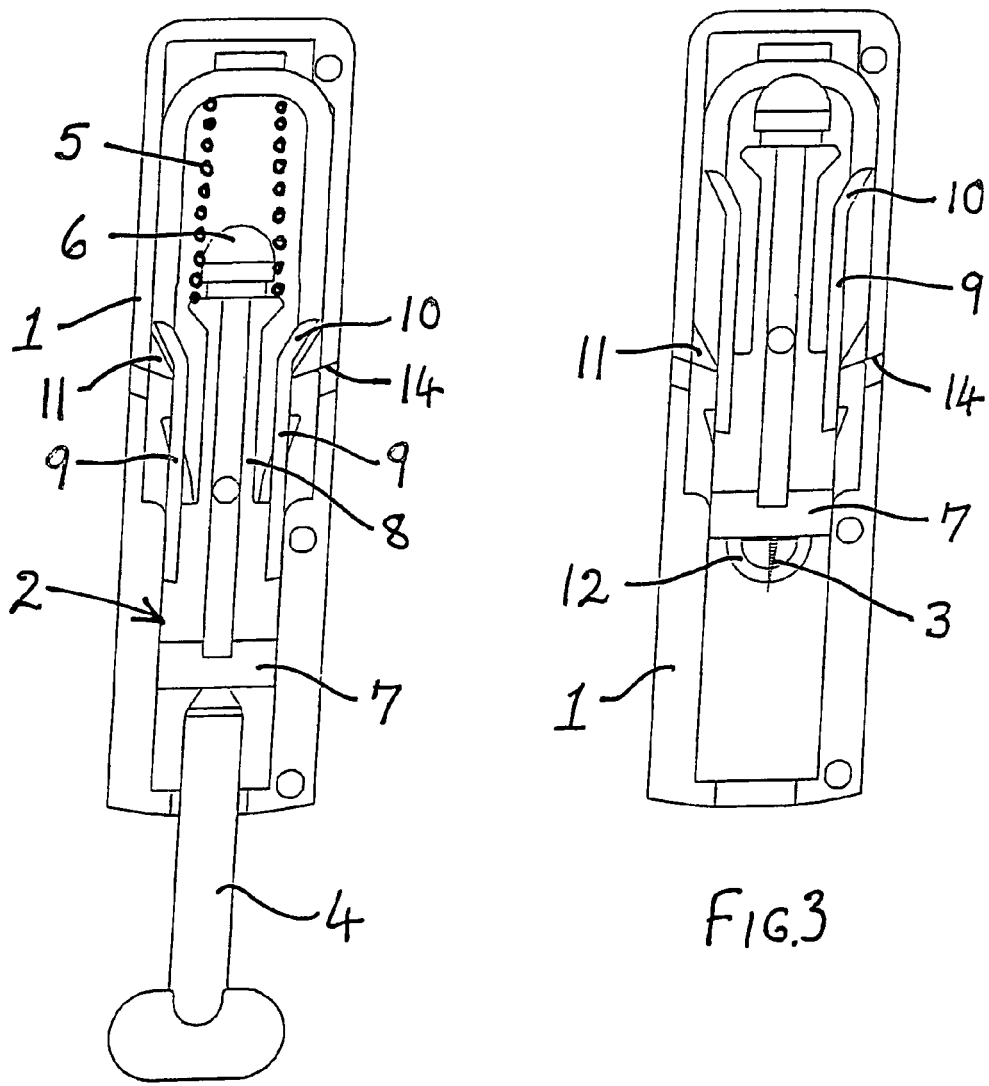
FIG. 2 is an axial section of the skin pricker of FIG. 1 in an initial state.

The device of FIGS. 1 and 2 has a barrel 1 of two halves joined at a longitudinal split to hold a lancet 2. The lancet has a plastics body encasing a needle 3 (FIG. 3) whose tip is initially embedded in a twist-off elongate cap 4 moulded integrally with the body. A spring 5 which drives the lancet forwards is shown only in FIG. 2. The spring acts on the head 6 of the lancet 2.

The lancet body has a large end portion 7 non-rotatably guided in the forward part of the barrel 1. A stem 8 extends rearwardly from the portion 7 terminating in the head 6. At opposite sides of the stem fingers 9 lead outwardly and rearwardly from the roots of the shoulders at the transition between the portion 7 and the stem 8. The fingers 9 are integrally moulded with the plastics body, and are resiliently flexible and can act in a springlike fashion. The fingers 9 have outwardly splayed tips 10. At about its mid-length the interior of the barrel 1 are formed inwardly and forwardly angled barbs 11.

Figure 3:
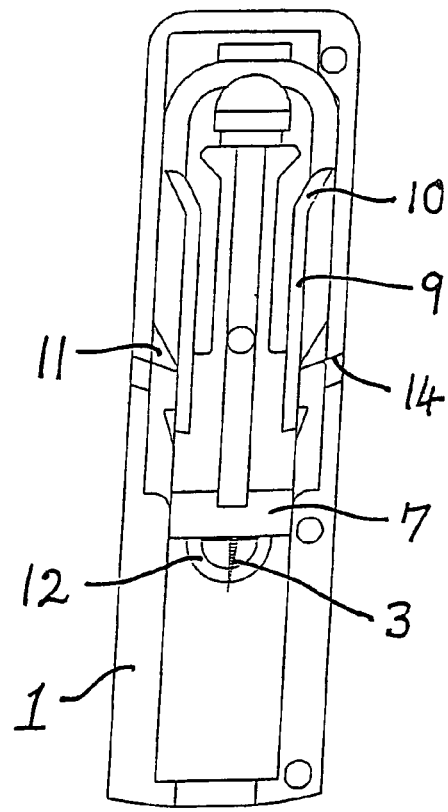
FIG. 3 is a similar section showing the lancet of the skin pricker in a cocked condition.
Figure 4:
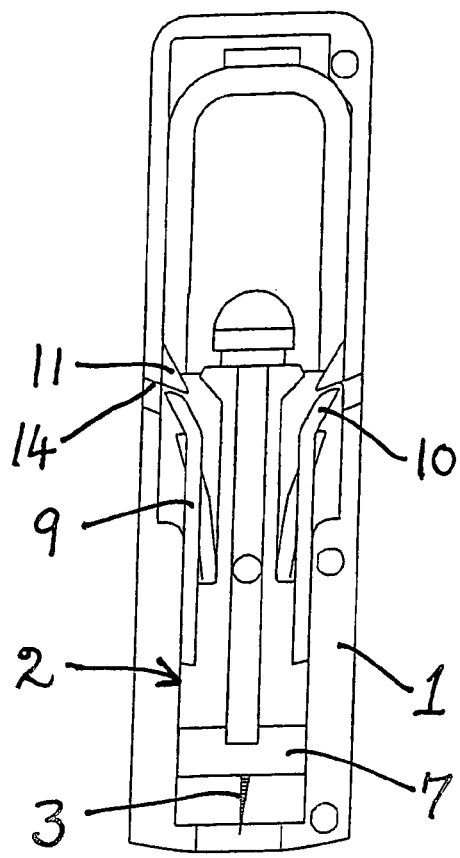
FIG. 4 is an axial section through the skin pricker after its lancet has been fired.
Figure 5:
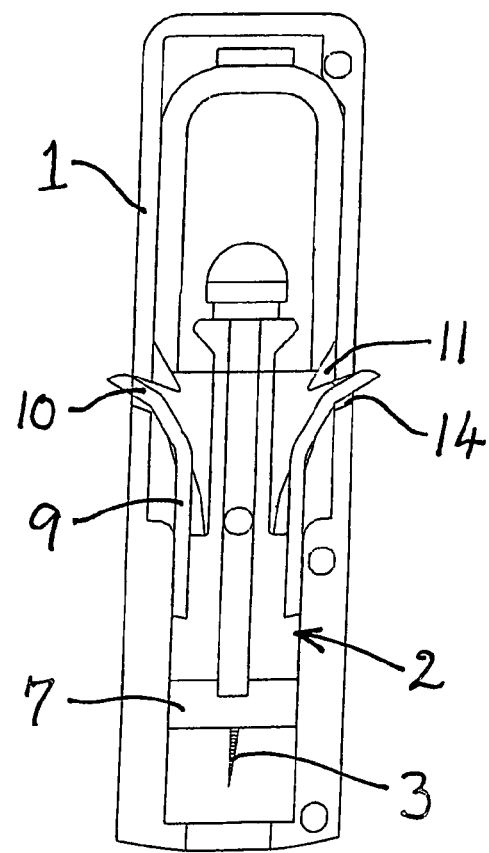
FIG. 5 is a similar section showing the skin pricker of FIG. 4 after an attempt has been made to re-cock the lancet.

Initially, with the spring relaxed, the tips 10 of the fingers 9 are behind the barbs 11. The cap 4 is pressed to retract the lancet, and the device is then cocked, as shown in FIG. 3, where the end portion 7 is locked behind a lug 12 of a trigger lever 13 (FIG. 1). The cap is twisted off and the device is applied and fired by pressing the trigger 13. The thrust of the spring urges the lancet forwards and the fingers 9 flex inwards as the tips 10 snap past the barbs 11, just before the needle tip momentarily emerges from the forward end of the barrel. As the over-extended spring 5 retracts, the tips 10 of the arms 9 engage behind the barbs 11 (the condition shown in FIG. 4). There is effectively a ratchet mechanism.

If the cap 4 is now used to try to push the lancet back into the cocked condition, while the main body of the lancet will move, at least initially, the fingers 9 are trapped. The fingers will flex as the tips 10 press against the barbs 11 until the arms bend and the tips 10 are pushed out through openings 14 in the side walls of the barrel 1 (the condition of FIG. 4). Thus the lancet is arrested and immobilised before the cocked position is reached, and re-firing is prevented.

In the embodiment described, the lancet is symmetrical, with spring arms 9 on opposite sides. While this is preferred, it would be possible to construct and guide the lancet in a manner such that only one arm would suffice.

The invention claimed is:
1. A disposable skin pricker, comprising:
an elongate housing having a forward end and a rearward end;
a longitudinally movable lancet carried in said housing and having a body and a lancet tip at a forward end, the lancet tip normally being within the housing;
a spring spring-loading said lancet;
a trigger mechanism to retain the lancet in a fully retracted position in which it energizes the spring, the trigger mechanism being actuable to release or fire the lancet to cause the lancet tip to have a momentary position projecting from the forward end of the housing; and
an arrangement for preventing re-use comprising a spring finger extending rearwardly from the lancet alongside but spaced from the body thereof, an abutment on the inside of the housing projecting inwardly past which a tip of the finger will snap during forward motion of the lancet, and an aperture disposed in the side wall of the housing such that any attempt to push the lancet back with a greater than a predetermined force after firing results in the abutment deflecting the tip of the finger out through said aperture to an exterior of the housing thereby to prevent return of said lancet to its fully retracted position.
2. The disposable pricker according to claim 1, wherein two fingers are on opposite sides of the lancet, and each finger inclines outwardly from the lancet body as well as extending rearwardly.

3. The disposable pricker according to claim 1, wherein the lancet tip is initially protected by an elongate cap by which the lancet is adapted to be pushed back to the fully retracted position from an initial pre-fired position in which each finger tip is immediately to the rear of the associated abutment or abutments.

4. The disposable pricker according to claim 1, wherein the lancet is symmetrical, with two fingers on opposite sides thereof.

5. The disposable pricker according to claim 4, wherein each finger is generally parallel to and spaced from the adjacent part or parts of the body of the lancet but with the finger tip flaring outwardly.

6. The disposable pricker according to claim 4, wherein each finger inclines outwardly from the lancet body as well as extending rearwardly.

7. The disposable pricker according to claim 4, wherein the housing has two opposed apertures and abutments.

8. The disposable pricker according to claim 7, wherein each finger inclines outwardly from the lancet body as well as extending rearwardly.

9. The disposable pricker according to claim 7, wherein the abutments are shaped as barbs pointing inwards and forwards.

10. The disposable pricker according to claim 9, wherein each finger inclines outwardly from the lancet body as well as extending rearwardly.

* * * * *

UNITED STATES PATENT AND TRADEMARK OFFICE
CERTIFICATE OF CORRECTION

PATENT NO. : 8,425,547 B2  Page 1 of 1
APPLICATION NO. : 10/547127
DATED : April 23, 2013
INVENTOR(S) : Marshall et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1302 days.

Signed and Sealed this

Eighth Day of September, 2015

Michelle K. Lee
*Director of the United States Patent and Trademark Office*